United States Patent [19]
Kirkovits et al.

[11] Patent Number: 5,929,276
[45] Date of Patent: Jul. 27, 1999

[54] PROCESS FOR THE PREPARATION OF ANHYDROUS TRISODIUM CITRATE

[76] Inventors: August Ernst Kirkovits, A2153, Stronegg 21; Josef Gass, A-2265 Drosing, Waltersdorfer Strasse 15, both of Austria

[21] Appl. No.: 09/055,470

[22] Filed: Apr. 6, 1998

Related U.S. Application Data

[63] Continuation-in-part of application No. 08/655,085, Jun. 3, 1996, abandoned.

[30] Foreign Application Priority Data

Jun. 6, 1995 [AT] Austria ................................. A 959/95

[51] Int. Cl.$^6$ ................................................. C07C 59/265

[52] U.S. Cl. .............................................. 562/584

[58] Field of Search ............................................... 562/584

[56] References Cited

U.S. PATENT DOCUMENTS

| | | | |
|---|---|---|---|
| 3,646,689 | 3/1972 | Kuchenthal et al. | 34/182 |
| 4,085,516 | 4/1978 | Jukkola et al. | 34/10 |
| 4,104,806 | 8/1978 | Reusch | 34/10 |

OTHER PUBLICATIONS

Hawley's Condensed Chemical Dictionary, twelfth edition, p. 1053, 1993.

The Merck Index, eleventh edition, p. 1360, 1989.

*Primary Examiner*—Samuel Barts
*Assistant Examiner*—Rosalynd Keys
*Attorney, Agent, or Firm*—Paul and Paul

[57] ABSTRACT

The invention relates to a process for producing anhydrous trisodium citrate the structure of which is unchanged as compared to a crystalline hydrate form, the anhydrous trisodium citrate, as well as its use as a carrier for inorganic and/or organic substances, in particular after being impregnated with liquids.

11 Claims, 2 Drawing Sheets

PROCESS FOR THE PREPARATION OF ANHYDROUS TRISODIUM CITRATE

CROSS-REFERENCE TO RELATED APPLICATION

This is a continuation-in-part of expending U.S. Pat. application Ser. No. 08/655,085 filed Jun. 3, 1996 now abandoned.

BACKGROUND OF THE INVENTION

1. Field of the Invention

The present invention relates to anhydrous trisodiumcitrate the structure of which is unchanged as compared to a crystalline hydrate mode, and to this material as a carrier for inorganic and/or organic substances, in particular after being impregnated with liquids.

2. Brief Description of the Prior Art

Trisodiumcitrate is obtained by neutralizing citric acid with caustic soda solution and allowing it to crystallize as hydrate mode, several hydrate forms being known. The dihydrate is the technically most important one of these hydrate forms. Trisodiumcitrate dihydrate is used in food industry as pH-regulator, complexing agent, stabilizer, synergist for antioxidation, and as a salt for cheese-making, to name but a few applications.

Because of an increased demand for environmentally acceptable washing agents, trisodiumcitrate dihydrate has been in use for some time as a builder for non-phosphate washing agents. It has the effect of preventing calcium salt deposits on the laundry, enhancing the effects of tensides, adjusting the alkalinity of the washing liquor, and improving the properties of the washing agent powder.

SUMMARY OF THE INVENTION

It has now been found that crystalline trisodiumcitrate hydrates can be dewatered by heating in a controlled manner to give anhydrous products. The structure of these products remains unchanged as compared to that of the parent hydrate, in other words to products which are porous. Thus, these products have a substantial internal surface. The porosity of the product can be as much as about 15%, if trisodium citrate dihydrate is used as the starting material.

These products maintain their pourability and flow properties over a long period of time, have by far shorter dissolution times as compared to the hydrate form, and may be mixed with any other product, i.e. with dry substances as well as with liquids, without subsequent formation of lumps, as is the case when using hydrates. Thus, the anhydrous products may be impregnated with liquids of inorganic or organic basis and serve as their carriers, but remain dry and pourable as such.

Thus, the present invention provides a process for preparing a porous anhydrous trisodiumcitrate from crystalline hydrated trisodium citrate, the structure of the anhydrous product being substantially unchanged as compared to a crystalline hydrated trisodium citrate. The process comprises heating the crystalline hydrated trisodium citrate feedstock in a controlled manner. The process includes heating the feedstock during a first period from about 145 degrees C. to at least about 175 degrees C. at a heating rate no greater than about 1.5 degrees C. per minute. The process further comprises subsequently maintaining the temperature of the feedstock of a temperature of at least about 175 degrees C. during a second period. Preferably, the heating rate is from about 0.5 to 1.5 degrees C. per minute during the first period, such as about 1 degree C. per minute. It is also presently preferred that the temperature of the feedstock be maintained at from about 180 to 185 degrees C. during the second period, such as about 180 degrees. It is also preferred that the feedstock be maintained at a temperature of at least about 175 degrees C. during the second period until the trisodium citrate has lost substantially all water of hydration. Preferably, the feedstock is heated until the residual water content is less about than 2 percent by weight. It is especially preferred that the feedstock be heated until the residual water content is less than about 0.5 percent by weight.

While the process of the present invention can be carried out using any type of equipment known to the art, it is presently preferred that the feedstock be maintained in motion while being heated, and that a stream of heated air is caused to move through the feedstock as the feedstock is in motion. This can be accomplished using a fluidized bed drier.

The present invention also provides an anhydrous trisodium citrate product. Preferably, this product has a porosity of about 15 percent by volume. The anhydrous trisodium citrate product can be impregnated with another substance, including various liquids and other materials, so that the product can be used as a carrier for such other substances. The high porosity of the anhydrous trisodium citrate product advantageously provides substantial carrying capacity.

DETAILED DESCRIPTION

Dewatering of the crystalline hydrates employed in the process of the present invention may be carried out in any industrial mixer, e.g. in a heated ödige mixer, but the preferred method is fluidized bed drying, as mechanical surface abrasion may be kept low in this way, and as a result of the short drying periods, which are, for instance, not more than about 30 min at a fluidizing air temperature of about 250° C.

Production Example

In a Lödige mixer some 1.25 kg of water were eliminated from 10 kg of trisodiumcitrate hydrate at a product temperature of 150–190° C. within 60 minutes.

The porous anhydrous sodium citrate of the present invention can be used as a carrier for a variety of substances, including organic and inorganic liquids such as hydrogen peroxide, tensides, surfactants, and the like.

Application Example 1

The product obtained in the production example (8.75 kg) was mixed with 1 kg of 60 $H_2O_2$ at room temperature, which became completely absorbed after some 30 min. The dry product had a content of 6% $H_2O_2$ (2.67% active oxygen). After six weeks of storage, the product was still pourable without the occurrence of a decrease in the peroxide content.

Application Example 2

1 kg of trisodiumcitrate anhydrate was mixed with 100 g of DEHYPON LS4 (tenside of the Henkel company) for some 15 min., resulting in a perfectly pourable product.

Application Example 3

1 kg of trisodiumcitrate anhydrate was mixed with 10 g of DEHYDOL LS4 (tenside of the Henkel company) for some 15 min, resulting in a perfectly pourable product.

Comparison

Application example 3 was repeated with trisodiumcitrate dihydrate; the product was not pourable.

Application Example 4

1 kg of trisodiumcitrate anhydrate was mixed with 1 kg of citric acid anhydrate and submitted to a storage test for 6 weeks. After this time the product was still perfectly pourable.

Comparison

Application Example 4 was repeated with trisodiumcitrate dihydrate; after 6 weeks the product was completely lumpy.

Comparison of Solubility

The following Table I compares the dissolution times in minutes in water at 25° C. of anhydrous trisodiumcitrate on the one hand, and trisodiumcitrate dihydrate on the other hand, both having the same grain size distribution:

TABLE 1

| Amount of salt added (weight per cent) | Anhydrous trisodium citrate | Trisodium citrate dihydrate |
|---|---|---|
| 10 | 0.46 | 1.05 |
| 30 | 0.59 | 2.14 |

Thus, the anhydrous salt dissolves much more quickly than the dihydrate salt.

Application Example 5

In order to illustrate the effect of the process of the present invention on the particle size distribution of the resulting anhydrous product, crystalline trisodium citrate dihydrate was heated according to the process of the present invention, using a Lodige plowshare mixer Type DVT 50 with a heating jacket, as detailed in Table II below, to give Product A.

Figure 1:
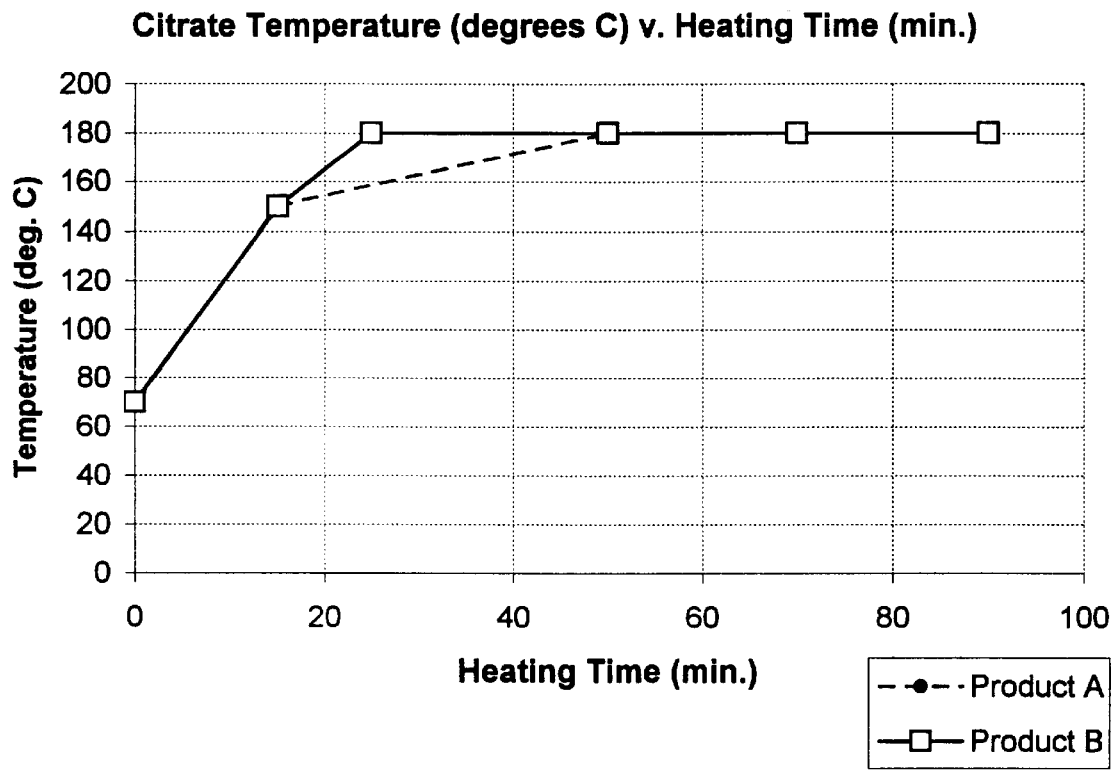
FIG. 1 is a graph plotting the temperature of trisodium citrate as a function of heating time for a product made according to the process of the present invention (Product A) and a comparative product (Product B) prepared according to a conventional process.
Figure 2:
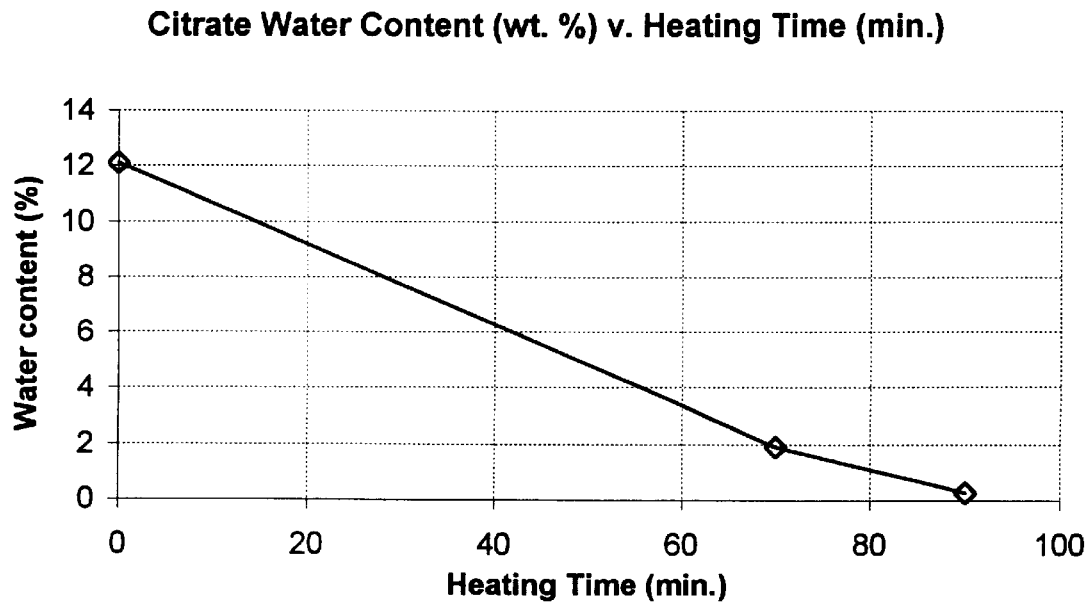
FIG. 2 is a graph plotting the water content of the trisodium citrate of Product A as a function of heating time.

The heating rate data given in Table II are illustrated in FIG. 1, while the water content data given in Table I are shown in FIG. 2. The particle size distribution of the feedstock and Product A are given in Table II and shown in the three-dimensional bar charts of FIGS. 3 and 4.

For comparison, the process was repeated, except that a constant rate of heating of 3 degrees C. per minute was employed to raise the temperature from 150 degrees C. to 180 degrees C. in 10 minutes, giving Product B.

Figure 3:
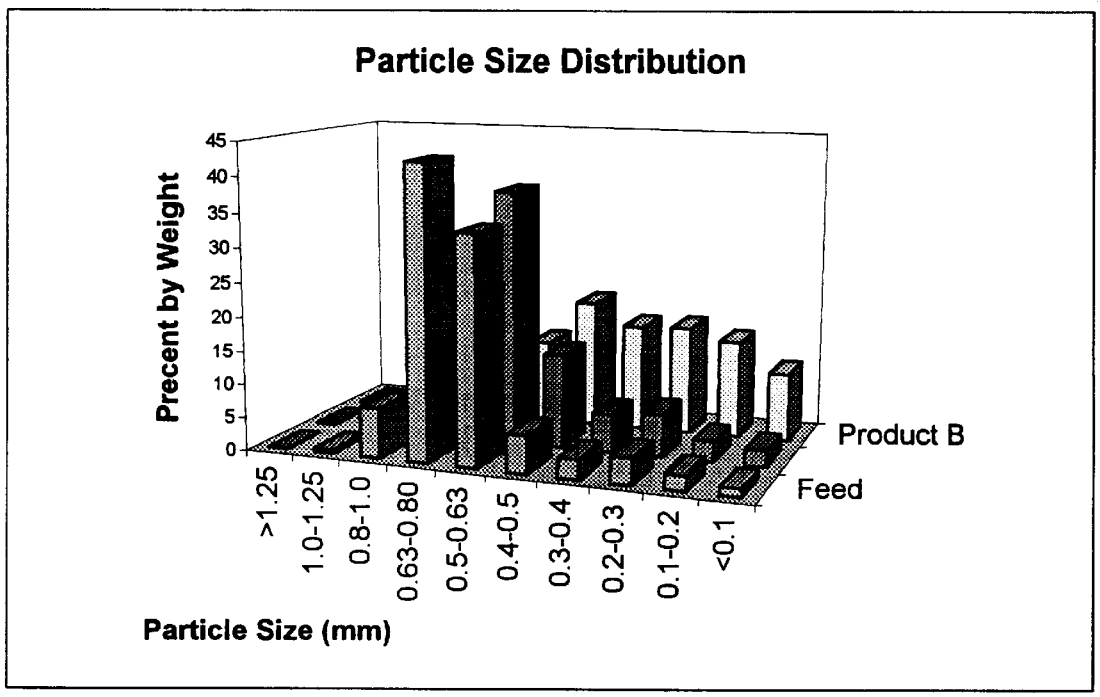
FIGS. 3 and 4 are three dimensional bar charts showing the particle size distributions of Products A and B, and the trisodium citrate dihydrate feedstock used to prepare Products A and B, showing the weight percent of particles as a function of size classifications. These two bar charts show the same data viewed from different perspectives.
Figure 4:
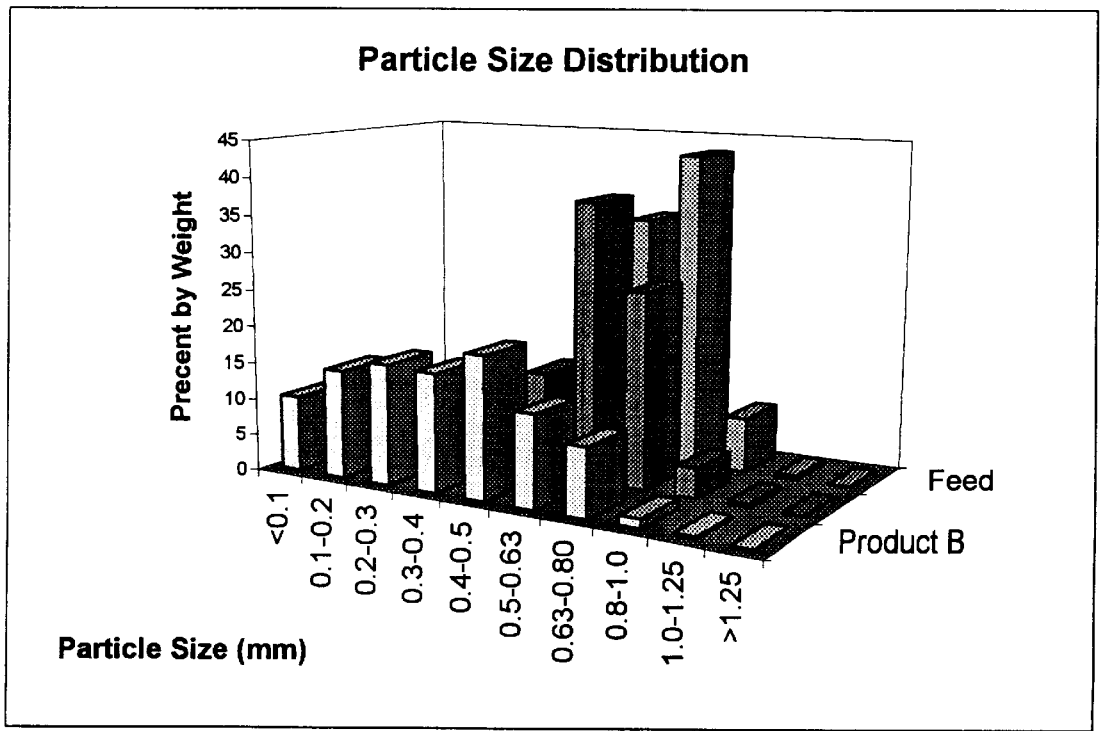

The heating rate data for Product B are shown in FIG. 1, and the particle size distribution for Product B is given in Table III and illustrated in FIGS. 3 and 4.

As can be easily seen in the bar charts, when anhydrous trisodium citrate is prepared according to the process of the present invention, the particle size distribution of the product is very similar to that of the dihydrate feedstock. Conversely, when the feedstock is heated rapidly in the conventional manner to drive off the water of hydration, the original crystalline structure is lost, as reflected in as the substantially different particle size distribution.

Comparison of the particle size distribution of Product B with that of Product A shows that Product B has a substantially greater proportion of finer particles, with about five times as many particles with a particle size between 0.1 and 0.2 mm, and about four times as many particles having a particle size less than 0.1 mm.

TABLE II

| | |
|---|---|
| Feed Trisodiumcitrate-Dihydrate (water content 12.09%) | 10 kg |
| mixer speed | 15 rpm |
| starting temperature | 70° C. |
| constant rate heating time 70° C.–150° C. | 15 min. |
| constant rate heating time 150° C.–180° C. | 35 min. |
| dwell time 180° C. | 40 min. |
| residual water content after 20 minutes at 180° C. | 1.9% $H_2O$ |
| residual water content after 40 minutes at 180° C. | 0.25% $H_2O$ |
| end product | 8.82 kg |

TABLE III

| | Percentage by Weight | | |
|---|---|---|---|
| Particle Size | Feedstock | Product A | Product B |
| >1.25 mm | 0.02 | 0.03 | 0.03 |
| 1.0–1.25 mm | 0.50 | 0.44 | 0.30 |
| 0.8–1.00 mm | 7.47 | 4.04 | 1.27 |
| 0.63–0.80 mm | 42.73 | 26.40 | 9.25 |
| 0.5–0.63 mm | 33.56 | 37.47 | 12.52 |
| 0.4–0.50 mm | 5.58 | 14.04 | 19.21 |
| 0.3–0.40 mm | 2.93 | 5.67 | 16.04 |
| 0.2–0.30 mm | 3.87 | 6.35 | 16.35 |
| 0.1–0.20 mm | 2.21 | 3.13 | 14.72 |
| >0.10 mm | 1.13 | 2.43 | 10.31 |
| Total | 100.00 | 100.00 | 100.00 |

The anhydrous trisodium citrate Product A of the present invention has superior properties compared with the trisodium citrate dihydrate feedstock ("F"), as exemplified by the data presented in Table IV, which gives the dissolution times (in minutes) in water of the feedstock and Product A as a function of temperature and amount of salt added (percent by weight). As can be seen from inspection of the Table, the anhydrous salt dissolves more quickly.

TABLE IV

| | 25° C. | | 30° C. | | 40° C. | | 60° | |
|---|---|---|---|---|---|---|---|---|
| % salt added | A | F | A | F | A | F | A | F |
| 1 | 0.37 | 0.43 | 0.30 | 0.41 | 0.24 | 0.28 | 0.16 | 0.20 |
| 5 | 0.40 | 0.51 | 0.35 | 0.50 | 0.27 | 0.31 | 0.20 | 0.25 |
| 10 | 0.46 | 1.05 | 0.39 | 1.02 | 0.31 | 0.40 | 0.25 | 0.30 |
| 20 | 0.53 | 1.36 | 0.45 | 1.30 | 0.34 | 0.53 | 0.29 | 0.38 |
| 30 | 0.59 | 2.14 | 0.53 | 1.55 | 0.42 | 1.04 | 0.35 | 0.49 |

Various modifications can be made in the details of the various embodiments of the process of the present invention, all within the scope and spirit of the invention and defined by the appended claims.

We claim:

1. A process for preparing a porous anhydrous trisodium-citrate from crystalline hydrated trisodium citrate, the structure of the anhydrous product being substantially unchanged as compared to a crystalline hydrated trisodium citrate, the process comprising:

(a) heating the crystalline hydrated trisodium citrate feedstock, the feedstock being heated during a first period from about 145 degrees C. to at least about 175 degrees C. at a heating rate no greater than about 1.5 degrees C. per minute, and subsequently, (b) maintaining the temperature of the feedstock of a temperature of at least about 175 degrees C. during a second period.

2. A process according to claim 1 in which the heating rate is from about 0.5 to 1.5 degrees C. per minute during the first period.

3. A process according to claim 2 in which the heating rate is about 1 degree C. per minute during the first period.

4. A process according to claim 1 in which the temperature of the feedstock is maintained at from about 180 to 185 degrees C. during the second period.

5. A process according to claim 4 wherein the temperature of the feedstock is maintained at about 180 degrees during the second period.

6. A process according to claim 1 wherein the feedstock is maintained at a temperature of at least about 175 degrees C. during the second period until the trisodium citrate has lost substantially all water of hydration.

7. A process according to claim 6 wherein the feedstock is heated until the residual water content is less than about 2 percent by weight.

8. A process according to claim 7 wherein the feedstock is heated until the residual water content is less than about 0.5 percent by weight.

9. A process according to claim 1 wherein the feedstock is maintained in motion while being heated.

10. A process according to claim 9 wherein a stream of heated air is caused to move through the feedstock as the feedstock is in motion.

11. A process for preparing anhydrous trisodiumcitrate from crystalline hydrated trisodium citrate, the structure of the anhydrous product being unchanged as compared to a crystalline hydrated trisodium citrate, the process comprising:

(a) heating the crystalline hydrated trisodium citrate feedstock, the feedstock being heated during a first period from about 145 degrees C. to at least about 175 degrees C. at a heating from about 0.5 to 1.5 degrees C. per minute, and subsequently;

(b) maintaining the feedstock at a temperature of from about 180 to 185 degrees C. during a second period until the trisodium citrate has lost substantially all water of hydration.

\* \* \* \* \*

UNITED STATES PATENT AND TRADEMARK OFFICE
CERTIFICATE OF CORRECTION

PATENT NO. : 5,929,276
DATED : July 27, 1999
INVENTOR(S) : August Ernst KIRKOVITZ and Josef GASS It is certified that error appears in the above-identified patent and that said Letters Patent is hereby corrected as shown below:

Column 1, Line 6, the word "expending" is corrected to "copending".

Signed and Sealed this

Fifteenth Day of February, 2000

Attest:

Q. TODD DICKINSON

Attesting Officer

Commissioner of Patents and Trademarks